United States Patent [19]
Canavaggio et al.

[11] Patent Number: 5,866,350
[45] Date of Patent: Feb. 2, 1999

[54] METHOD FOR THE IMMUNOLOGICAL DETERMINATION OF A BIOLOGICAL MATERIAL IN A SAMPLE

[75] Inventors: Michel Etienne Canavaggio, Paris; Helen Hwai-an Lee, Elancourt, both of France

[73] Assignee: Helen Hwai-An Lee, United Kingdom

[21] Appl. No.: 355,992

[22] Filed: Dec. 14, 1994

Related U.S. Application Data

[63] Continuation of Ser. No. 972,313, Nov. 5, 1992, abandoned, which is a continuation of Ser. No. 417,880, Oct. 10, 1989, abandoned, which is a continuation of Ser. No. 936,582, Nov. 12, 1986, abandoned.

[30] Foreign Application Priority Data

Mar. 19, 1985 [FR] France .................................. 85 04013

[51] Int. Cl.$^6$ ...................................................... C12Q 1/56
[52] U.S. Cl. ................................ 435/13; 435/7.4; 436/69
[58] Field of Search ..................................... 435/7.2, 7.24, 435/7.25, 7.32, 7.9, 4, 7.92–7.95, 13, 28, 29, 805, 970, 973, 7.4; 436/63, 69, 66, 518, 530, 805, 811; 424/11

[56] References Cited

U.S. PATENT DOCUMENTS

| | | | |
|---|---|---|---|
| 4,166,765 | 9/1979 | Weetal | 435/26 |
| 4,496,654 | 1/1985 | Katz et al. | 435/7.9 |
| 4,591,570 | 5/1986 | Chang | 436/518 |
| 4,608,246 | 8/1986 | Bayer et al. | 424/11 |
| 4,696,805 | 9/1987 | Yamashita et al. | 435/7.9 |
| 4,729,961 | 3/1988 | Avrameas et al. | 436/501 |
| 5,210,017 | 5/1993 | Carlsson et al. | 435/7.8 |

OTHER PUBLICATIONS

G. Brown, "Application of Immunologic Assays to the Coagulation Laboratory," in Clinics in Laboratory Medicine vol. 4 No. 2 pp. 345–361 (1984).

D. Pollet et al, "Enzyme–Antigen Immunoassay for Human Placental Alkaline Phosphatase . . . " in Clinical Chemistry vol. 31 No. 1 pp. 41–45 (1985).

*Primary Examiner*—Carol A. Spiegel
*Attorney, Agent, or Firm*—Bierman, Muserlian and Lucas

[57] ABSTRACT

A method for determining a cell surface antigen comprising
  (a) immobilizing an antibody specific for the cell surface antigen to be determined on a solid phase;
  (b) immobilizing sample cell suspected of containing said cell surface antigen with the solid-phase antibody to bind the cell surface antigen and antibody;
  (c) the solid phase is washed after incubation; and
  (d) the presence of the cell surface antigen is detected by means of a property inherent to the cell by cellular enzymatic activity.

3 Claims, 4 Drawing Sheets

METHOD FOR THE IMMUNOLOGICAL DETERMINATION OF A BIOLOGICAL MATERIAL IN A SAMPLE

PRIOR APPLICATION

This application is a continuation of U.S. patent application Ser. No. 972,313 filed Nov. 5, 1992 which is a continuation of U.S. patent application Ser. No. 417,880 filed Oct. 10, 1989 which is a continuation of U.S. patent application Ser. No. 936,582 filed Nov. 12, 1986, all now abandoned.

FIELD OF THE INVENTION

The present invention relates to a method for identifying, and eventually assaying, biological materials.

DESCRIPTION OF THE PRIOR ART

There are many existing methods for detecting biological materials. Of these methods, the most common are haemagglutination, fluorescent, enzymic or radioactive immunoassays.

The immunoassays mentioned above require the use of artificial coupling products, such as antibody-enzyme conjugates, or radioactive labelling.

SUMMARY OF THE INVENTION

The present invention relates to a method which does not resort to artificial coupling products or radioactive products and which, in distinction to haemagglutination, may be carried out in the solid phase. This method possesses, in particular, the advantage of being simple and rapid, and of being able to be automated while being very sensitive.

The present invention relates more especially to a method for determining a biological material in a sample, characterized in that:

a) a ligand having a binding affinity for the said biological material is immobilized on a solid phase;

b) the sample is incubated in the presence of the said solid phase on which the ligand is immobilized;

c) the solid phase is washed after incubation; and d) the presence of the said biological material, bound to the solid phase by way of the ligand, is revealed with the aid of a property inherent in the said biological material.

The method according to the present invention makes it possible to demonstrate all biological materials which will hereinafter be referred to as "auto-revealable", that is to say, any biological product which possesses an inherent property which can be directly or indirectly demonstrated for detection by man or machine.

Auto-revealable materials are, in particular, materials possessing a natural coloration, for example red cells, or possessing a special appearance under artificial radiation, or alternatively materials which are capable, either directly when the material is a macromolecule or as a result of certain components, for example an endogenous enzyme or a chemical component, contained in the materials, of colouring a substrate, or of generating fluorescence or luminescence, protein C for instance.

The auto-revealable materials can naturally be revealed through many other chemical or physical properties.

In general, the method according to the present invention is more particularly intended for detecting biological materials which can be directly visualized in natural or artificial light. In this case, it concerns generally coloured or pigmented materials which are present in high concentration.

This method is, in addition, especially attractive for detecting biological materials which can be indirectly revealed through a coloration or an endogenous enzymic reaction in the presence of a substrate and, where appropriate, after enzyme activation or cell lysis if the materials are cells, with endogenous enzymes, in particular peroxidase, phosphatase, galactosidase, glucose oxidase transaminase, for example, being released.

The auto-revealable biological materials can be:

1) Cells, in particular:
   red cells for the determination of the blood groups, the ABH, Lewis, P; Lutheran, rhesus (D, C, c, E, e) Kell, Duffy, Kidd and MNSs or other systems, which can be revealed through their coloration or, after lysis, through the peroxidase activity on a substrate;
   leukocytes; polynuclear leukocytes, lymphocytes, monocytes;
   blood platelets;
   cells of normal or pathological epithelial, endothelial, connective tissue origin, present in the withdrawal fluid or withdrawn by cell puncture or biopsy and resuspended in an artificial buffer.

2) Microorganisms: bacteria, parasites, viruses, the bacteria being, for example, revealable after lysis through the activity of endogenous enzymes such as galactosidase.

3) Biological macromolecules, and especially enzymes or molecules endowed with enzyme activity, such as haemoglobin, transaminases, phosphatases, proteases and clotting factors, for example. An example (Example 5) is given hereinafter with the plasma protein C.

The auto-revealed product can be directly in active form, or can be secondarily activated by cell lysis and released in the reagent medium, or by secondary activation in an enzyme cascade, as is the case for the clotting enzymes.

The solid phase can be any support customarily used for immunoassay, the support being in the form of either beads, wells on microtitration plates, reactive strips or the like. This support can be made of any polymer of natural or synthetic origin, or of an amorphous material such as glass. Advantageously, membranes of nitrocellulose or nylon are used for the reactive strips, and polyvinyl, polypropylene, polystyrene or other plastics for the beads or microplates. Gels or particles based on agarose, acrylamide or latex can also be used.

The sensitization of the solid phase with the ligand which has an affinity for the material to be assayed is accomplished either by passive adsorption or by covalent coupling, depending on the nature of the support and the requirements of the test. After adsorption of the ligand, the solid phase can be saturated with proteins or macromolecules such as bovine albumin, foetal calf serum or gelatin, or chemically modified by chemical agents such as TWEEN, to prevent non-specific interactions. This solid phase can be modified for storage in desiccated or lyophilized form. The ligand can be a lectin, an antigen or, most frequently, an antibody.

In an especially advantageous embodiment of the invention, the solid phase consists of a reactive strip or a plate sensitized with at least two different ligands, specific for different biological materials which are capable of being present in the sample to be tested, for example a ligand for group A red cells and a ligand for group B red cells. In this case, by bringing this strip or plate into contact whith a blood sample, the blood group can be determined immediately, the corresponding area appearing coloured.

Each area containing a ligand can incorporate a designation, by means of which the nature of the outcome can be identified by man or machine, an alphanumeric code or bar code, for example, being used.

To facilitate the use of such supports, it is also possible to deposit the different ligands on the strip according to a specific scheme, for example in the form of a letter or a sign in relationship to the phenotype in question.

Thus, strips can be provided on which the anti-A antibodies are in the shape of an A, the anti-B antibodies in the shape of a B and the anti-AB antibodies in the shape of AB. In this manner, the attachment of the red cells to the specific antibody enables the phenotype, which appears in the shape of a red letter, to be read directly.

This system enables a blood grouping to be determined in approximately five minutes, which cannot be achieved by any known method.

The auto-revealable biological materials are incubated in the presence of the solid phase in an aqueous medium. This medium can be a normal or pathological biological fluid, such as blood, serum, plasma, urine, cerebral spinal fluid or a pleural, peritoneal, synovial or other effusion fluid, or an isotonic artificial medium optionally containing optimization substances (proteins, salts, macromolecules, chemical agents such as TWEEN or polyethylene sorbitan monostearate in which the specimen is resuspended. Incubation is performed at room temperature or at a modified temperature with or without agitation for a period which will depend on the nature of the material and its capacity to bind to the ligand. After incubation, the liquid phase is removed by phase separation or washing, for example, in a solution such as a 0.05% strength TWEEN/PBS buffer.

The method according to the present invention can be used more especially for demonstrating phenotypes of red cells corresponding to surface antigens, using, by way of a ligand, the corresponding monoclonal antibodies.

The revelation of the binding of the red cells can be direct, as a result of the red coloration which appears, or alternatively, to make the method more sensitive, the cells bound after washing are lysed with a haemolysing agent and an enzyme activity, especially peroxidase activity, of the lysate is assayed. The assay of peroxidase is known, a chromogenic substrate such as orthophenylenediamine (OPD) or tetramethyl benzidine (TMB) being usable.

Figure 1:
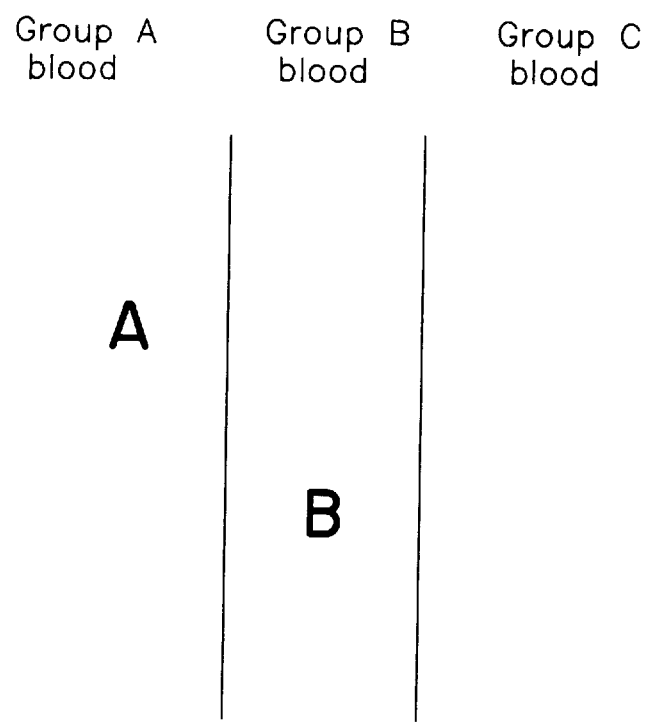
FIG. 1 is an illustration of the blood type grouping of Example 2.

The advantage of using the peroxidase activity of haemoglobin resides in the fact that, although there are many other enzymes in red cells, deficiencies are always possible, whereas a complete or very substantial deficiency of haemoglobin would be lethal.

The samples below are intended to illustrate other characteristics and advantages of the method according to the present invention.

EXAMPLE 1

Determination of the Blood Group in the ABH System

Purified anti-A and anti-B monoclonal antibodies are passively adsorbed on a rigid Immulon microtitration plate of the Microelisa plate type with U-shaped wells, Laboratory Dynatech reference M 124 B, or a flexible PVC microtitration plate with U-shaped wells, reference M 24 of the same Laboratory. Anti-(A+B) antibodies can also be used. For this purpose, the purified monoclonal antibodies are incubated at a concentration of 4 $\mu$g/ml in 0.1M bicarbonate buffer pH 9.6 for three hours at 37° C., in the proportion of 100 $\mu$l per well, the late being covered over with an adhesive film. The plate is saturated for 30 minutes with a 10% strength solution of foetal calf serum.

Samples of whole blood of groups A, B, AB or O, withdrawn into a tube containing EDTA, citrate or heparin, as well as 1% strength blood cell suspensions of weak groups $A_2$, $A_3$, $A_x$, $A_{end}$, $B_{3, A1}B_4$ and cis AB, are distributed in the proportion of 100 $\mu$l per cup and incubated at room temperature for 30 minutes.

The plate is washed by automatic washing, using a Dynatech Multiwash for 4 cycles, with 0.15M PBS buffer pH 7.4 containing 0.05% of TWEEN 20. The reaction can be read spontaneously for the groups A and AB red cells with the anti-A antibodies, and for the groups B and AB red cells with the anti-B antibodies.

This positive reaction is brought about through a macroscopic adsorption of the red cells on the surface of the cups coated with antibody, no red cell being visible in the case of a negative reaction (for example with red cells of group O). To make the reading more sensitive or make it objective, the reaction can be revealed, after lysis of the red cells, by the peroxidase reaction of haemoglobin. To this end, a haemolysing solution containing a substrate for peroxidase is added into the cups: 3 mg/ml of orthophenylenediamine (OPD) in 0.1M citrate in the presence of $H_2O_2$ and containing 0.1% of saponin as haemolysing agent. After 10 minutes, the reaction is stopped by adding 50 $\mu$l of 1.5M $H_2SO_4$. The reactions are read in a spectrophotometer at 490 nm.

In this example, the specimens containing the different normal groups or weak groups (with few antigenic sites) give positive reactions greater than 1.5 optical density units, and the very weak groups, having very few antigenic sites particularly ($A_x$, $A_{end}$, $A_1B_x$, cis AB) give an optical density of between 0.15 and 1.5, or exceeding 1.5. The background in this experiment is less than 0.050.

Table I gives an example of a result in comparison with the classical agglutination technique. The results are expressed in OD at 490 nm for the test according to the invention, and scored as a number of plusses according to the intensity as is conventional for agglutination.

TABLE 1

Reactivity of a spectrum of red cells of different phenotypes, measured as OD (upper line), and in agglutination, scored as plusses (lower line)

|        | $A_1$ | $A_2$ | $A_3$ | $A_3$ | $A_x$ | $A_x$ | $A_{end}$ | B | $B_3$ | $A_1B_x$ | CisAB | O |
|--------|-------|-------|-------|-------|-------|-------|-----------|---|-------|----------|-------|---|
| Anti-A | 1.5   | 1.5   | 1.5   | 1.5   | 0.184 | 0.822 | 0.647     | 0.002 | 0.005 | 1.5   | 1.5   | 0.000 |
|        | +++   | +++   | +++   | +++   | −     | (+)   | (+)       | −     | −     | +++   | +++   | −     |
| Anti-B | 0.004 | 0.001 | 0.005 | 0.002 | 0.000 | 0.001 | 0.000     | 1.5   | 1.5   | 0.380 | 1.5   | 0.000 |
|        | −     | −     | −     | −     | −     | −     | −         | +++   | +++   | −     | −     | −     |

These results show that the technique of the invention is of greater sensitivity, this technique being capable of detecting unambiguously samples of weak groups or uncommon groups such as $A_x$, $A_{end}$, $A_1B_x$ or cis AB, whereas these are only faintly detected or negative in agglutination. The method according to the invention for determining the ABH groups has been validated in comparison with the agglutination method on 2,000 blood specimens taken from blood donors, and on samples of rare red cells selected for their low density of antigenic sites or uncommon feature.

EXAMPLE 2

Determination of the Blood Groups of the ABH System on a Nitrocellulose or Nylon Membrane 1) Preparation of the Membranes Strips of nylon type Biodyne TM membrane from Laboratoire Pall are cut to the desired sizes. If the test is carried out in Kahn tubes, the strips can be cut to the internal dimensions of the tube.

The membrane is sensitized with anti-A and anti-B monoclonal antobodies, which are deposited in liquid form, either with a pipette or with a pad impregnated with the antibody solution. So as to identify the reaction which takes place, an A-shaped pad for the anti-A and a B-shaped pad for the anti-B are placed on the membrane. The deposition can also be carried out in the form of other identification signs or codes which can be read by the operator or by a machine. If purified antibodies are used, the latter are deposited at a concentration of 10 μg/ml, or, possibly, at a different concentration, according to the experimental results. Diluted ascites fluids, or culture supernatants containing the antibody, can also be used.

The membranes are dried for two hours at room temperature or 30 minutes at 37° C. in a drying oven. After being dried, the membrane is washed with PBS buffer at pH 7.4 and then saturated with a protein solution such as 1% strength bovine albumin in PBS buffer or with 10% strength foetal calf serum or 1% strength gelatin.

At this stage, the membranes can be used at once stored, after desiccation, for subsequent application.

2) Actual Grouping Test

The sensitized strips are immersed in a tube containing whole blood or a blood cell suspension for three minutes at room temperature with or without agitation. At the end of the incubation period, they are rinsed with 0.15M sodium chloride solution and read immediately. If the blood is of group A, the letter A appears, as a result of the binding of the red cells; if the blood is of group B, the letter B appears; if the group is AB, both letters appear; if the cells are of group O, the strip remains completely white (FIG. 1).

The process according to the invention applies also to the detection in the human serum or plasma of anti-erythrantigen antibodies. In the following, firstly a first method of carrying out said process will be illustrated. It concerns a sandwich test where antibodies to be detected are immunoadsorbed on the solid phase sensitized by erythrantigens and revealed by the specific fixation of human red cells. This first method is illustrated in Example 3.

EXAMPLE 3

Detection of Anti-A, Anti-B or Anti-AB Antibodies

The A or B erythrantigens are passively adsorbed on a rigid "Immulon" microtitration plate of the Microelisa plate type with U-shaped wells, laboratory Dynatech reference M 124B, or a flexible PVC microtitration plate with U-shaped wells, reference M 24 of the same Laboratory.

The A or B antigens can originate from different sources:

soluble antigens, of human origin, which are present in the saliva of some subjects or extracted from mucus in particular of ovarian cysts.

antigens of animal origin, such as the horse or the pig (extracted from the gastric mucus).

antigens extracted from the membrane of human red cells of group $A_1$, $A_2$, B or AB. In such a case, stromas of red cells are prepared (for instance, according to the method described by GARDAS A. and KOSCISLAK J., in Vox Sang., 1971, 20, 2, 137–149). The erythrantigens are extracted from the membrane for 15 minutes at 4° C. in the presence of a 2% w/v strength solution of octylglucoside (SIGMA Laboratory) and of a 5% v/v strength ammonia. Others dissociating agents can be used, such as TRITON X 100 (octylphenoxy polyethoxy ethanol) at a concentration of 1%. However, the preparation is centrifuged for 30 minutes at 15 000 g in order to remove the insoluble material.

This antigen raw extract can be used directly after dilution in 0.05M phosphate buffered at pH 7.4 to sensitize the microtitration plates or to be submitted to additional purification steps.

synthetic antigen possibly coupled to a macromolecular substrate, such as bovine albumin.

anti-idiotype antibodies can also be used to sensitize the solid phase.

For the passive adsorption on the microtitration plates, the antigens are diluted to a concentration in the region of 10 μg/ml in 0.1% M 0.05M phosphate buffered at pH 7.4 for the antigens extracted from erythrocyte membranes, or in 0.% M bicarbonate buffer pH 9.6 for soluble antigens.

For this purpose, the antigen dilution is incubated for 3 hours at 37° C. in the proportion of 200 μl per well, the plate being covered over with an adhesive film.

The plate is saturated for 30 minutes with a 10% strenght solution of foetal calf serum or a 1% strength solution of bovine albumin. After washing of the plate in a 0.15M PBS buffer pH 7.4 containing 0.05% of TWEEN 20, the plasma or serum samples to be studied are distributed in the proportion of 150 μl per well, then a Red blood cell solution containing 2% of phenotypes $A_1$, $A_2$, B, AB or O is added in the proportion of 50 μl per well. In order to sensitize the reaction, the Red blood cells can be treated by enzymes such as papain.

The plate is incubated for 30 minutes at room temperature, then washed by automatic washing during 4 cycles in a 0.15 PBS buffer pH 7.4 containing 0.05% of TWEEN 20.

The reactions can be read spontaneously for anti-A, anti-B or anti-AB serums, respectively with $A_1$ and $A_2$ red cells for the anti-A, B for the anti-B, $A_1$, $A_2$ or B for the anti-AB.

This positive reaction is brought about through a macroscopic adsorption of red cells on the surface of the cups coated with antibody, no red blood cells being visible in the case of a negative reaction (for example with red cells of group O). To make the reaction more sensitive or make it objective, the reaction can be revealed, after lysis of red cells, by the peroxidase reaction of haemoglobin. To this end, a haemolysing solution containing a substrate for peroxidase is added into the cups: 3 mg/ml of orthophenylenediamine (OPD) in 0.1M citrate buffer at pH . . . in the presence of $H_2O_2$ and containing 0.1% of saponin as haemolysing agent. After 10 minutes, the reaction is stopped by adding of 50 μl of 1.5M $H_2SO_4$. The reactions are read in a spectrophotometer at 490 nm.

Figure 2:
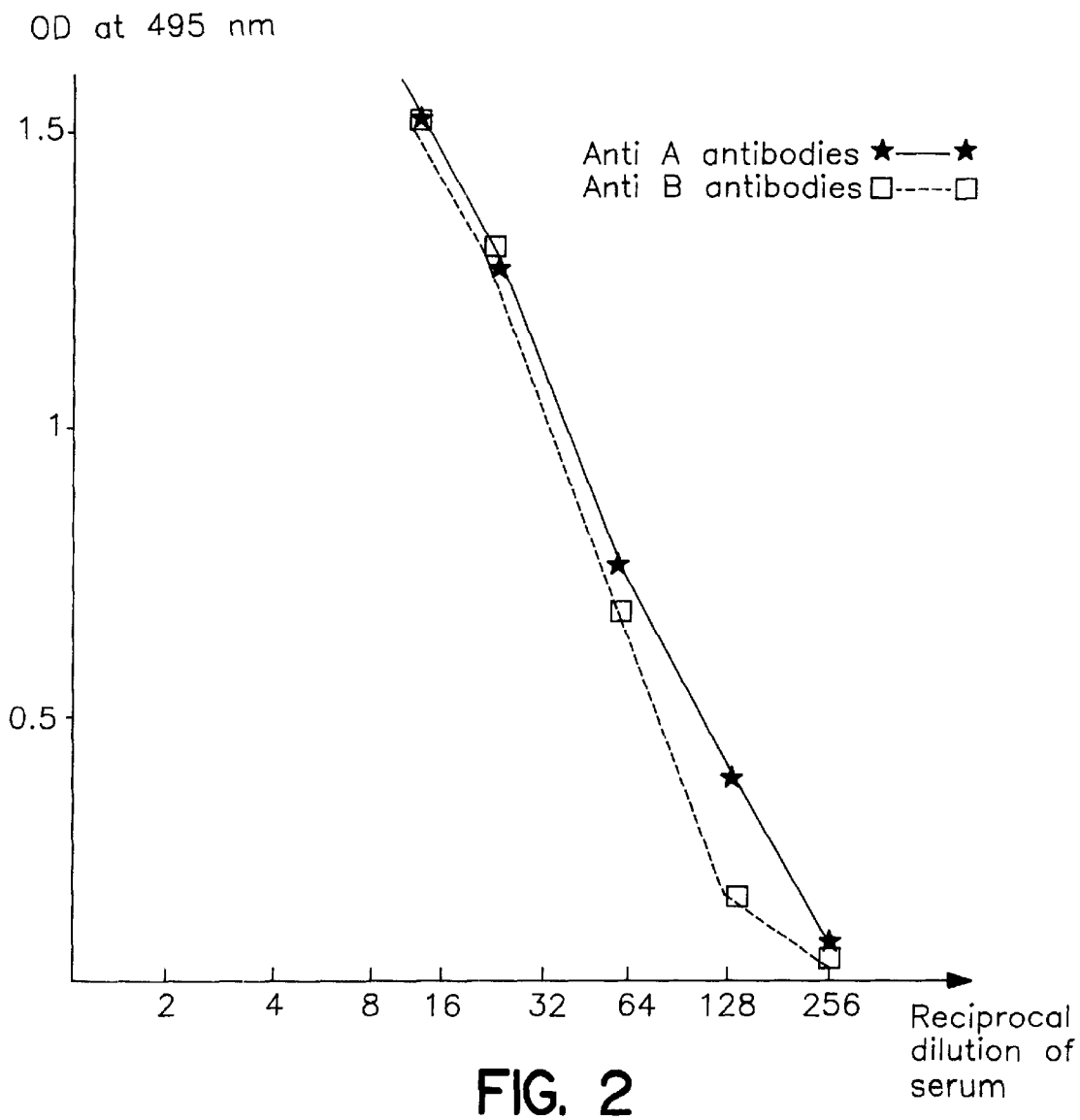
FIG. 2 is a diagram of the results of the Example 3 for the detection of antibodies.

FIG. 2 is a diagram illustrating the results which are obtained with the method (method I) of Example 3 in the case of the titration of a serum containing an anti-A antibody and of a serum containing an anti-B antibody, respectively. The reciprocal dilution of serum has been laid off as abscissa and the optical density (OD) at 495 nm has been laid off as ordinate. This FIG. 2 shows that the sensitivity of the titration is at least equal to that of the standard agglutination technique in tubes.

The process for detecting anti-erythrantigen antibodies can also be carried out by a second method, which constitutes a test in two steps wherein the sample containing the anti-red cell antibody to be detected is incubated in the presence of human red cells of various phenotypes. After removal of the antibodies which have not reacted with the red cells (by passing through a macromolecular filter or by washing), the red cells are incubated with a solid phase coated with human anti-immunoglobuline, in such a way to retain specifically on the solid phase only the red cells which have reacted with the antibodies to be detected. This method can substitute with more sensitivity and with a quantitative result for the detection by Coombs test of anti red cell antibodies possibly present in the serum of some patients or blood donors and which could, in the absence of detection, involve haemolytic accidents after transfusion. This method II is illustrated in Example 4.

EXAMPLE 4

Detection of Anti Rhesus D Antibodies

Human anti-immunoglobulin antibodies, purified by affinity chromatography, or monoclonal antibodies recognizing the human IgG and IgM or a mixture of human anti IgG and anti IgM, are passively adsorbed on a microtitration plate of the Microelisa type with U-shaped or V-shaped wells. To this end, the antibodies are incubated at a concentration of 10 μg/ml in 0.1M bicarbonate buffer pH 9.6 for 3 hours at 37° C. in the proportion of 100 μl per well. The solid phase is washed by automatic washing in 0.15M PBS buffer pH 7.4 containing 0.05% of TWEEN 20.

Simultaneously, a mixture with equal parts of a suspension containing 2% of red cells of phenotype Rhesus D is incubated for 5 to 10 minutes with the plasma or serum in which anti Rhesus D antibodies are searched. The so incubated red cells are, after washing in saline solution or filtration on a macromolecular solution, brought into contact with the microtitration plate coated with human anti-immunoglobuline for an incubation of 30 minutes at room temperature.

The plates are washed by automatic washing with 0.15M PBS pH 7.4 containing 0.05% of TWEEN 20.

The reactions can be read spontaneously for the sera containing anti Rhesus D antibodies with red cells carrying Rhesus D antigens.

The positive reactions are brought about through a macroscopic adsorption of the red cells on the surface of the cups coated with antibody; in the case of a negative reaction, no red cell is visible. To make the reading more sensitive or make it objective, the reaction can be revealed, after lysis of the red cells, by the peroxidase reaction of haemoglobin. To the end, a haemolysing solution containing a substrate for peroxidase is added into the cups. 3 mg/ml of orthophenylenediamine (OPD) in 0.1M citrate buffer in the presence of $H_2O_2$ and containing 0.1% of saponin as haemolysing agent. After 10 minutes, the reaction is stopped by adding 50 μl of 1.5M $H_2SO_4$. The reactions are read in a spectrophotometer 490 nm.

Figure 3:
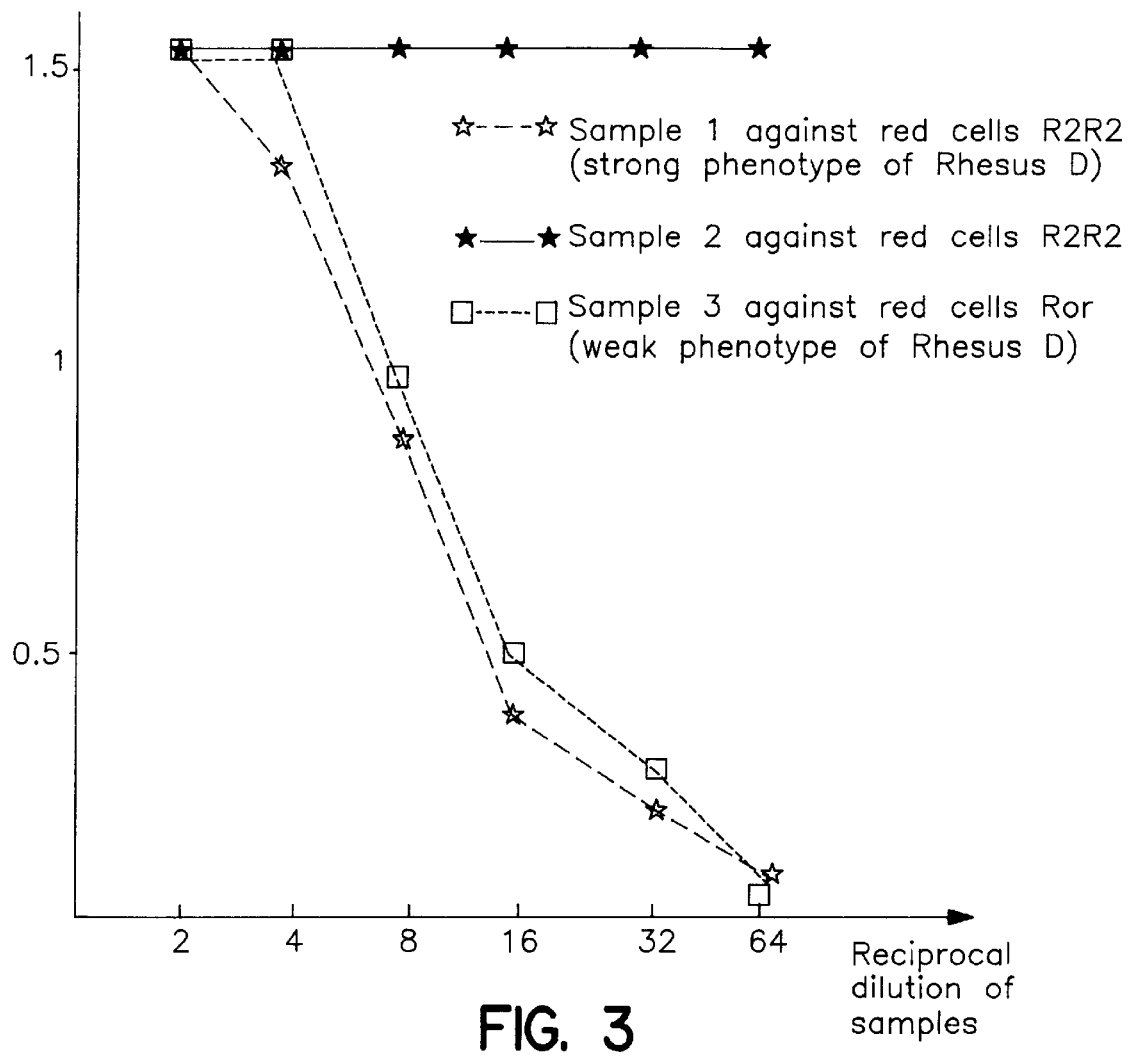
FIG. 3 is a diagram of the results of Example 4 for the detection of antibodies.

FIG. 3 is a diagram illustrating the results obtained with the method (method II) of Example 4. For the aessays reported on FIG. 3, three samples of serums previously brought to a dilution corresponding to the last positive dilution according to the Coombs method were used. As on FIG. 2, the values of the dilution have been laid off as abscissa and the optical density OD measured at 495 nm has been laid off as ordinate. The curves laid off on FIG. 3 show that the process according to the present invention is at least thirty two times more sensitive than the Coombs method of titration of anti Rhesus D antibodies.

The process according to the present invention can also be used to the dosage of the biological activity of plasma protein C.

This application is illustrated by the following Example 5.

EXAMPLE 5

Purified anti protein C monoclonal antibodies are passively adsorbed on a microtitration plate of the Microelisa type, Laboratory Dynatech reference M 124B, or on divisible small bars, reference M 1798 A of the same firm.

For this purpose, the purified monoclonal antibodies are incubated at the optimal concentration (5 to 10 μg/ml) in 0.1M bicarbonate buffer pH 9.6 for 3 hours at 37° C., in the proportion of 200 μl per well, the plate being covered over with an adhesive film. After washing of the plate in 0.15M PBS buffer pH 7.4 containing 0.1% of TWEEN 20, the samples of plasma or the dilutions of the same in 0.5M TBS Tris buffer (Tris Buffered Saline); 0.1M NaCl, 1% of bovine albumin, pH 7.35 are incubated in the proportion of 200 μl for 30 minutes at 37° C.

After washing with the same procedure as in Example 1, the immuno-adsorbed protein C is activated in the presence of 6 mM human thrombin-rabbit Trombomoduline complexes in 0.15M TBS buffer, pH 7.35+9 mM $CaCl_2$. This activating solution is distributed in the proportion of 200 μl and allowed to incubate for 30 minutes at 37° C. After washing with the same procedure than in Example 1, 200 µl of substrate are added in each cup (1 mM substrate 2366 (from KABI Diagnostic) in 0.05M Tris buffer 0.15M NaCl, pH 8.3).

The reaction is stopped after one hour by adding acetic acid at a final concentration of 15%.

The dosage of Example 5 has been applied to normal or pathological plasmas.

Figure 4:
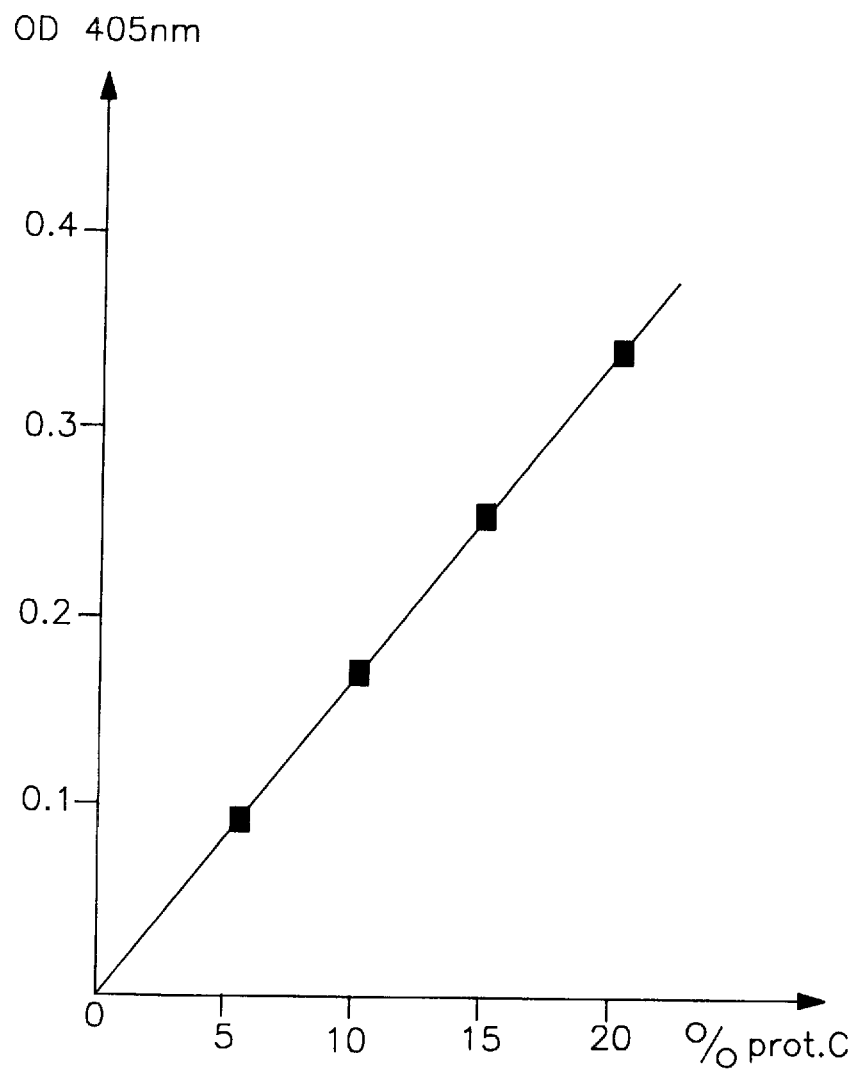
FIG. 4 is a graph of the concentration of protein C obtained in Example 5.

A pool of 20 normal human plasmas is taken as a reference for 100% of protein C. Four dilutions of this reference corresponding to protein C concentrations of 20%, 15%, 10% and 5% are introduced in the assay in order to obtain the reference curve. The negative check sample 0% is constituted by a plasma previously freed from protein C by immunoadsorption. The reference curve is represented (FIG. 4). FIG. 4 is a diagram on which the protein C concentration expressed in percentage, of a normal plasma have been laid off as abscissa and the optical density OD, read at 405 nm, has been laid off as ordinate.

Six groups of plasma samples have been tested in order to estimate the clinical interrelation of the test of the present invention by comparison with a standard sandwich ELISA test of quantitative dosage.

The results are presented in Table II.

The results obtained with the test according to the present invention are closely interrelated to the clinic and to the quantitative results of the ELISA test. Further on, the test according to the invention allows to detect the qualitative deficits in protein C (deterioration of the biological activity of the enzyme without quantitative deficit) that the ELISA dosage cannot render evident because this last test is only quantitative.

The process according to the invention can also be carried out with alternative modes.

So plasma protein C can be activated before the distribution of the samples in the microtitration wells or also in the course of the first incubation of the samples. In such a case, the substrate is directly added after washing of the solid phase. Also, the activation may be carried out with thrombin, taken alone or with other enzymic activators and, particularly, certain enzymes extracted from snacke venom (for example the venom RVVX of the firm SIGMA). It is also possible to use a fluorescent substrate.

TABLE II

| Studied group | Plasma number | Average concentration in protein C by ELISA | Average concentration in protein C by the process according to the invention |
|---|---|---|---|
| I Normal subjects | 5 | 98% | 91% |
| II Subjects with anti vitamin K | 5 | 15% | 18% |
| III Congenital deficits in Protein C | 7 | 37% | 44% |
| IV Congenital deficits in Protein C + anti vitamin K | 8 | 11% | 14% |
| V Congenital deficits in coagulation factors other than Protein C | 6 | 92% | 97% |
| VI Qualitative deficit in Protein C | 2 | 105% | 17% |

What we claim is:

1. A method of determining the concentration of a coagulation factor of the intrinsic or extrinsic pathway of the coagulation cascade in a sample, comprising the sequential steps of:

(a) providing a solid phase with an immobilized ligand having a specific binding affinity for said coagulation factor;

(b) contacting said sample with the immobilized ligand to bind any said coagulation factor in said sample to said solid phase;

(c) washing the solid phase of step (b) to remove any unbound sample;

(d) reacting both a chromogenic or fluorogenic substrate specific for said coagulation factor and an activator for said coagulation factor with the washed solid phase of step (c) in order to generate a chromogen or fluorophor; and (e) measuring the amount of the chromogen or the fluorophor produced by step (d) in order to determine the concentration or said coagulation factor in said sample.

2. The method according to claim 1, wherein the ligand is a monoclonal antibody.

3. The method of claim 1 wherein the coagulation factor is plasma protein C.

* * * * *